US007167734B2

(12) United States Patent
Khalil et al.

(10) Patent No.: US 7,167,734 B2
(45) Date of Patent: Jan. 23, 2007

(54) METHOD FOR OPTICAL MEASUREMENTS OF TISSUE TO DETERMINE DISEASE STATE OR CONCENTRATION OF AN ANALYTE

(75) Inventors: Omar S. Khalil, Libertyville, IL (US); Shu-jen Yeh, Grayslake, IL (US); Stanislaw Kantor, Buffalo Grove, IL (US); Charles F. Hanna, Libertyville, IL (US); Eric B. Shain, Glencoe, IL (US)

(73) Assignee: Abbott Laboratories, Abbott Park, IL (US)

( * ) Notice: Subject to any disclaimer, the term of this patent is extended or adjusted under 35 U.S.C. 154(b) by 323 days.

(21) Appl. No.: 09/834,440

(22) Filed: Apr. 13, 2001

(65) Prior Publication Data

US 2003/0023151 A1 Jan. 30, 2003

(51) Int. Cl.
*A61B 5/00* (2006.01)
(52) U.S. Cl. ............... 600/310; 600/473; 600/476
(58) Field of Classification Search ........ 600/309–310, 600/322–324, 316, 331; 356/39–42
See application file for complete search history.

(56) References Cited

U.S. PATENT DOCUMENTS 4,655,225 A 4/1987 Dähane et al.

(Continued)

FOREIGN PATENT DOCUMENTS

WO 95/04924 2/1995

(Continued)

OTHER PUBLICATIONS

Braverman, "The Cutaneous Microcirculation: Ultrastructure and Microanatomical Organization", *Microcirculation*, vol. 4, No. 3, 1997, pp. 329-340.

(Continued)

*Primary Examiner*—Eric F. Winakur
(74) *Attorney, Agent, or Firm*—David L. Weinstein (57) ABSTRACT

A method for collecting optical data at two morphologically similar, substantially non-overlapping, and preferably adjacent, areas on the surface of a tissue, while the temperature in each area is being maintained or modulated according to a temperature program. The optical data obtained are inserted into a mathematical relationship, e.g., an algorithm, that can be used to predict a disease state (such as the diabetes mellitus disease state) or the concentration of an analyte for indicating a physical condition (such as blood glucose level). This invention can be used to differentiate between disease status, such as, for example, diabetic and non-diabetic. The method involves the generation of a calibration (or training) set that utilizes the relationship between optical signals emanating from the skin under different thermal stimuli and disease status, e.g., diabetic status, established clinically. This calibration set can be used to predict the disease state of other subjects. Structural changes, as well as circulatory changes, due to a disease state are determined at two morphologically similar, but substantially non-overlapping areas on the surface of human tissue, e.g., the skin of a forearm, with each area being subjected to different temperature modulation programs. In addition to determination of a disease state, this invention can also be used to determine the concentration of an analyte in the tissues. This invention also provides an apparatus for the determination of a disease state, such as diabetes, or concentration of an analyte, such as blood glucose level, by the method of this invention.

7 Claims, 4 Drawing Sheets

U.S. PATENT DOCUMENTS

| | | | |
|---|---|---|---|
| 4,882,492 A | 11/1989 | Schlager | |
| 4,975,581 A | 12/1990 | Robinson et al. | |
| 5,009,230 A | 4/1991 | Hutchinson | |
| 5,028,787 A * | 7/1991 | Rosenthal et al. | 250/339.12 |
| 5,057,695 A | 10/1991 | Hirao et al. | |
| 5,068,536 A | 11/1991 | Rosenthal | |
| 5,077,476 A | 12/1991 | Rosenthal | |
| 5,082,787 A | 1/1992 | Nolte et al. | |
| 5,086,229 A | 2/1992 | Rosenthal et al. | |
| 5,204,532 A | 4/1993 | Rosenthal | |
| 5,209,231 A | 5/1993 | Cote et al. | |
| 5,218,962 A * | 6/1993 | Mannheimer et al. | 600/331 |
| 5,237,178 A | 8/1993 | Rosenthal et al. | |
| 5,284,139 A | 2/1994 | Khalil et al. | |
| 5,321,265 A | 6/1994 | Block | |
| 5,348,003 A | 9/1994 | Caro | |
| 5,362,966 A | 11/1994 | Rosenthal et al. | |
| 5,379,764 A | 1/1995 | Barnes et al. | |
| 5,419,321 A | 5/1995 | Evans | |
| 5,434,412 A | 7/1995 | Sodickson et al. | |
| 5,460,177 A | 10/1995 | Purdy et al. | |
| 5,492,118 A | 2/1996 | Gratton et al. | |
| 5,497,769 A | 3/1996 | Gratton et al. | |
| 5,513,642 A | 5/1996 | Ostrander | |
| 5,551,422 A | 9/1996 | Simonsen et al. | |
| 5,632,273 A | 5/1997 | Suzuki | |
| 5,666,956 A | 9/1997 | Buchert | |
| 5,676,143 A | 10/1997 | Simonsen et al. | |
| 5,725,480 A | 3/1998 | Oosta et al. | |
| 5,755,226 A | 5/1998 | Carim et al. | |
| 5,800,347 A * | 9/1998 | Skates et al. | 600/300 |
| 5,844,239 A | 12/1998 | Kimura | |
| 5,893,364 A | 4/1999 | Haar et al. | |
| 5,935,062 A | 8/1999 | Messerschmidt et al. | |
| 5,978,691 A | 11/1999 | Mills | |
| 6,334,065 B1 * | 12/2001 | Al-Ali et al. | 600/323 |

FOREIGN PATENT DOCUMENTS

| | | |
|---|---|---|
| WO | 99/55222 | 4/1999 |
| WO | 99/39631 | 8/1999 |
| WO | 99/59464 | 11/1999 |

OTHER PUBLICATIONS

Duda and Hart, *Pattern Classification and Scene Analysis*, John Wiley & Sons (1973), pp. 17-20.

Duda and Hart, *Pattern Classification and Scene Analysis*, John Wiley & Sons (1973), pp. 130-138.

James, et al., "Use of X-Ray Diffraction in Study of Human Diabetic and Aging Collagen", *Diabetes,* vol. 40, 1991, pp. 391-394.

King, et al., "Global Burden of Diabetes, 1995-2025", *Diabetes Care,* vol. 21, No. 9, 1998, pp. 1414-1431.

Monnier, et al., "Skin Collagen Glycation, Glycoxidation, and Crosslinking Are Lower in Subjects With Long-Term Intensive Versus Conventional Therapy of Type 1 Diabetes", *Diabetes* vol. 48, 1999, pp. 870-880.

Rendell, et al., "Diabetic Cutaneous Microangiopathy", *The American Journal of Medicine,* vol. 93, 1992, pp. 611-618.

Rendell et al., "Microvascular Blood Flow, Volume, and Velocity Measured by Laser Doppler Techniques in IDDM", *Diabetes,* vol. 38, 1989, pp. 819-824.

"Report of the Expert Committee on the Diagnosis and Classification of Diabetes Mellitus", *Diabetes Care,* vol. 20, No. 7, 1997, pp. 1183-1197.

Rohlfing, et al., "Use of GHb (HbA1c) in Screening for Undiagnosed Diabetes in the U.S. Population", *Diabetes Care,* vol. 23, No. 2, 2000, pp. 187-191.

Sibbald, et al., "Skin and Diabetes", *Endocrinology and Metabolism Clinics of North America,* vol. 25, No. 2, 1996, pp. 463-472.

Wiernsperger, "Defects in microvascular haemodynamics during prediabetes: contributor or epiphenomenon?", *Diabetologia,* vol. 43, 2000, pp. 1439-1448.

Wilson, et al., "Detection of microvascular impairment in type I diabetics by laser Doppler flowmetry", *Clinical Physiology,* vol. 12, 1992, pp. 195-208.

Wu, et al., "Noninvasive Determination of Hemoglobin and Hematocrit Using a Temperature-Controlled Localized Reflectance Tissue Photometer", *Analytical Biochemistry,* vol. 287, 2000, pp. 284-293.

U.S. Appl. No. 09/080,470, filed May 18, 1998.

U.S. Appl. No. 09/098,049, filed Nov. 23, 1998.

U.S. Appl. No. 09/419,461, filed Oct. 15, 1999.

Qu, et al., "Monte Carlo Modeling Studies of the Effect of Physiological Factors and Other Analytes on the Determination of Glucose Concentration In Vivo by Near Infrared Optical Absorption and Scattering Measurements", *Journal of Biomedical Optics,* vol. 2, No. 3, 1997, pp. 319-325.

PCT International Search Report.

\* cited by examiner

METHOD FOR OPTICAL MEASUREMENTS OF TISSUE TO DETERMINE DISEASE STATE OR CONCENTRATION OF AN ANALYTE

BACKGROUND OF THE INVENTION

1. Field of the Invention

This invention relates to an apparatus and method for the non-invasive diagnosis of a disease state or the non-invasive determination of concentrations of analytes in vivo.

2. Discussion of the Art

Diabetes mellitus is a chronic systemic disease in which the body either fails to produce or fails to respond to the hormone insulin, which regulates the metabolism of glucose. It is estimated that there are 16 million diabetics in the United States and 100 million diabetics worldwide. The growth rate in the number of diabetics is estimated at 11.5% annually. The number of diabetics is estimated to be as high as 154 million worldwide by the year 2000 (H. King, R. E. Aubert, and W. H. Herman, "Global burden of diabetes, 1995–2025 prevalence, numerical estimates and projections" Diabetes Care 1998;21:1414), and to exceed 200 million worldwide by the year 2010. A large number of diabetics remain undiagnosed. A method for screening for diabetes would be beneficial for early diagnosis and for starting treatment and management well before the onset of complications.

Diabetes is frequently associated with microangiopathy. Microangiopathy results from the effect of diabetes on microcirculation, which involves the small blood vessels such as capillaries, venules, arterioles, and shunts. Microangiopathy can lead to micro-vessel complications such as neuropathy (nerve damage), retinopathy (eye damage), and nephropathy (kidney failure). The expression "diabetic angiopathy" deals with effect of diabetes on the arterial as well as the other elements of the vascular system such as venules, veins, and lymph subsystem. The relationship between diabetes and impaired circulation has been known in the medical art for the past two decades. Laser Doppler flowmetry has been used to diagnose peripheral vascular disease and vascular complications in diabetic patients. Impaired circulation is manifested by a decrease in cutaneous blood flow and a decrease in response to temperature changes, i.e., cooling or warming of the skin.

There is growing evidence that microcirculatory defects can be detected well before detection of fasting hyperglycemia, i.e. high blood glucose level for a fasting subject (N. Wiernsperger, Diabetologia 2000; 43; 1439–1449). Laser Doppler flowmetry and capillary microscopy studies have indicated microcirculation disturbances due to diabetes and have shown differences in cutaneous blood flow between diabetics and non-diabetics (S. B. Wilson, "Detection of microvascular impairment in type 1 diabetes by laser Doppler flowmetry, Clinical Physiology, 1992; 12; 195). In diabetic subjects, heating of a body part, or contralateral cooling of a body part, resulted in impaired blood flow, as measured by laser Doppler flowmetry (M. Rendell et al, "Microvascular blood flow, volume and velocity measurements by laser Doppler techniques in IDDM" Diabetes; 1989: 819–824). However, these studies of capillary blood flow and laser Doppler flowmetry were reported for advanced stages of diabetes (M Rendell et al, "Diabetic cutaneous microangiopathy" American Journal of Medicine 1992; 93: 611). Additionally, X-ray crystallographic studies showed differences in structure of tissues of diabetic subjects, due to cross-linking of collagen fibers resulting from glycation (V. J. James et al., "Use of X-ray Diffraction in Study of Human Diabetic and Aging Collagen", Diabetes, Vol.40 (1991) 391–394).

Diabetes and certain other diseases cause structural changes to the skin that can affect the optical properties thereof, the response of these optical properties to changes in concentration of glucose or other analytes, and the response of these optical properties to cutaneous temperature changes. R. G. Sibbald et al., "Skin and Diabetes", Endocrinology and Metabolism Clinics of North America, Vol. 25, No. 2 (1996) 463–472, summarize a set of structural effects of the skin that are associated with diabetes. Included among these effects is thickened skin, which may relate pathophysiologically to accelerated collagen aging, with elastic fiber fraying and increased crosslinking, resulting from glycosylation of collagen fibers. Another effect of diabetes is "yellow skin", which also results from glycosylation of dermal collagen. Change in dermal collagen structure in diabetic patients has been also reported by V. M. Monnier et al., "Skin Collagen Glycation, Glycoxidation, and Crosslinking Are Lower in Subjects With Long-Term Intensive Versus Conventional Therapy of Type 1 Diabetes", Diabetes, Vol. 48 (1999) 870–880. Further, V. J. James et al., "Use of X-ray Diffraction in Study of Human Diabetic and Aging Collagen", Diabetes, Vol. 40 (1991) 391–394, shows that collagen skin fiber undergoes a structural change as a result of diabetes. The net effect of these findings is that there are structural differences, i.e., size, level of crosslinking, and distribution of collagen fibers, in the skin of diabetic subjects as compared with the skin of non-diabetic subjects. These differences result in a difference in the scattering characteristics of the skin of diabetic subjects.

In order to understand the effect of the structural differences between the skin of diabetics and that of non-diabetics on the measured optical signals, it is useful to examine the scattering of light in human tissue.

The scattering of light by human tissue can be approximated by an equation that expresses the reduced scattering coefficient $\mu'_s$ for a tissue or a turbid medium as:

$$\mu'_s = 3.28\pi a^2 \rho (2\pi a n_{medium}/\lambda)^{0.37}(m-1)^{2.09} \quad (1)$$

where "a" represents the average cell diameter, $\rho$ represents the number concentration of cells, "$n_{medium}$" represents the refractive index of interstitial fluid, $\lambda$ represents the wavelength, and m represents the ratio of the refractive index of the cells to that of the interstitial fluid ($m = n_{cells}/n_{medium}$). The scattering coefficient changes as cell size "a" or refractive index "$n_{medium}$" change. Temperature can affect the scattering coefficient by a change in cell diameter "a", a change in the number concentration of cells $\rho$, or a change in the refractive index mismatch "m". Because the diabetic status is independent of glucose concentration, i.e., a diabetic patient can have high or low blood glucose level, it is possible to assume that the diabetic status is independent of "m". However, differences in crosslinking of collagen for diabetics may lead to a different range for the dimensional parameter "a" between the diabetic and the non-diabetic groups. Differences in the variable "a" will lead to a difference in the scattering characteristics of the skin of diabetic subjects, because the scattering characteristics affect the term "a" in Equation (1). Thus, the response of the scattering coefficient to changes in glucose concentration, or other concentrations of analytes, and the response of the scattering coefficient to cutaneous temperature changes are expected to be different for diabetic subjects as compared to those responses of the same parameters determined for non-diabetic subjects.

Scattering properties of tissue can vary with temperature as a result of one or more of the following changes:

(a) an increase in temperature can decrease the refractive index of interstitial fluid and increase the scattering coefficient of tissue;

(b) an increase in temperature can change the refractive index of cell membranes;

(c) an increase in temperature can increase cell size, and hence, can increase the scattering coefficient.

In the case of (a) or (b), an increase in the refractive index mismatch "m" in Equation (1), which increases as the temperature increases, can also increase the scattering coefficient.

Methods of diagnosing diabetes typically require a large number of laboratory tests, such as, for example, successive blood glucose level measurements while the patient is in a fasting state, determination of serum glycated hemoglobin HbA1c, and oral glucose tolerance (or meal tolerance) tests. These tests are usually performed after clinical symptoms of diabetes are observed. These symptoms include thirst, fatigue, and frequent urination (Report of the Expert Committee on the Diagnosis and Classification of Diabetes Mellitus, Diabetes Care 1997; 20:117–135). The use of a glycated hemoglobin test has been equivocal in diagnosing diabetes, even though it is time-consuming and requires drawing of blood. See C. L. Rohlfing et al., "Use of HbA1c in screening for undiagnosed diabetes in US population", Diabetes Care 2000; 23: 187–191.

A non-invasive test for screening diabetics will save a great number of laboratory tests and will allow screening larger populations, even if clinical symptoms of diabetes are not evident. A non-invasive test will also allow early diagnosis and subsequent control of diabetes, which in turn will delay the onset of complications from diabetes. If uncontrolled, diabetes can result in a variety of adverse clinical manifestations, including retinopathy, atherosclerosis, microangiopathy, nephropathy, and neuropathy. In its advanced stages, diabetes can cause blindness, coma, and ultimately death.

Non-invasive determination of glucose has been the subject of several patents. U.S. Pat. Nos. 5,082,787; 5,068,536; 5,077,476; 5,086,229; 5,204,532; 5,237,178; 5,362,966 describe transmission measurements through the finger. U.S. Pat. Nos. 5,321,265; and, 5,434,412 describe Kromoscopic methods for the determination of glucose. U.S. Pat. Nos. 5,492,118 and 5,551,422 describe measurements based on light scattering. U.S. Pat. Nos. 4,655,225; 4,882,492; 5,460,177; 4,975,581 describe methods for the detection of glucose with light of long wavelength (>1100 nm) where glucose does, presumably, have stronger absorption bands. U.S. Pat. Nos. 5,009,230; 4,975,581; 5,379,764; 4,655,225; 5,893,364; 5,497,769; 5,209,231; and 5,348,003 describe a variety of optical methods for the non-invasive determination of blood glucose level in the human body.

U.S. Pat. No. 5,362,966 describes measurement of finger temperature away from the optical measurement area. WO 95/04924 describes a near infrared non-invasive measurement instrument, where light is introduced and measured at an extremity, such as a finger tip, while the temperature of the same extremity is measured at another location remote from the location of the optical measurement area. The temperature value measured is used in the calculation algorithm together with the optical data to determine the concentration of an analyte. The temperature at the measurement site is not controlled or varied according to a preset program. U.S. Pat. No. 5,551,422 describes a glucose sensor that is brought to a specified temperature, preferably somewhat above the body normal temperature, with a thermostatically controlled heating system. U.S. Pat. No. 5,666,956 describes a method for the determination of glucose from the infrared emission of the tympanic membrane. U.S. Pat. No. 5,978,691 describes a method of measuring changes in molecular behavior, induced by a change in thermal energy, to facilitate the measurement of physiological parameters in blood.

U.S. Pat. No. 5,844,239 describes a fiber-optics-based optical device for determination of the optical properties at a shallow depth in a tissue. The sensor comprises several unit fiber bundles. Each unit fiber bundle has a light introduction fiber and several light collection fibers arranged in concentric rings. Signals from each group of fibers at the same distance are detected to enhance the signal to noise ratio. Further, signals from the plurality of unit bundles are added up, or averaged, to further improve the signal to noise ratio. The temperature is not controlled at the positions where the unit bundles contact the skin. The temperature is not varied according to a preset program.

U.S. application Ser. No. 09/080,470, filed May 18, 1998, assigned to the assignee of this application, describes a sensor employing a temperature control for non-invasive determination of blood glucose level. U.S. application Ser. No. 09/098,049, filed Nov. 23, 1998, assigned to the assignee of this application, describes methods for determining optical properties of tissue having a plurality of layers non-invasively. Both applications disclose the use of a temperature controllable optical element that contacts the skin.

Cutaneous microcirculation occurs at depths of 1 to 2 mm below the epidermal surface of the skin (I. M. Braverman, "The Cutaneous Microcirculation: Ultrastructure and Microanatomical Organization", Microcirculation (1997) Vol. 4, No. 3, 329–340). Thus, measurement of optical properties of skin close to the surface thereof can provide useful information on the effect of blood circulation on the concentration of metabolites in tissues that are close to the surface of the skin. Also, studies of blood circulation close to the surface of the skin by means of laser Doppler flowmetry (referred to as LDF herein) have shown that laser Doppler flowmetry is a good tool for diagnosing peripheral circulatory disease. Laser Doppler flowmetry (LDF) measurements are restricted to the top-most layer of the skin (≈200 microns) because the beam loses its coherence due to scattering. Temperature dependence of laser Doppler flowmetry studies does not incorporate structural changes in the skin due to diabetes. Thus, a deficiency in the LDF prior art is the lack of inclusion of temperature dependence of scattering in the classification and diagnosis of diabetes complications.

Although a variety of detection techniques have been disclosed in the art, there is still no commercially available device that provides reliable non-invasive measurements of blood glucose level. As a result, current approaches to non-invasive metabolite testing, such as glucose monitoring, have not achieved wide acceptance.

SUMMARY OF THE INVENTION

This invention provides a method for collecting optical data at two morphologically similar, substantially non-overlapping, and preferably adjacent, areas on the surface of a human tissue, while the temperature in each area is being maintained or modulated according to a temperature program. The optical data obtained are inserted into a mathematical relationship, e.g., an algorithm, that can be used to predict a disease state (such as the diabetes mellitus disease state) or the concentration of an analyte for indicating a physical condition (such as blood glucose level).

This invention can be used to differentiate between disease status, such as, for example, diabetic and non-diabetic. The discovery underlying the method of this invention is that certain optical properties of human tissue change in response to changes in temperature of the tissue. The method involves the generation of a calibration (or training) set that utilizes the relationship between optical signals emanating from the skin under different thermal stimuli and disease status, e.g., diabetic status, established clinically. This calibration set can be used to predict the disease state of other subjects. Because thermal stimuli affect microcirculatory action within the capillary loops, the method depends upon measuring the optical properties of the tissue at different areas on the surface of the tissue, to a depth of up to two millimeters, as a function of thermal stimuli. Structural changes, as well as circulatory changes, due to a disease state are determined at two morphologically similar, but substantially non-overlapping areas on the surface of human tissue, e.g., the skin of a forearm, with each area being subjected to different temperature modulation programs. In addition to determination of a disease state, this invention can also be used to determine the concentration of an analyte in a human tissue. This invention also provides an apparatus for the determination of a disease state, such as diabetes, or concentration of an analyte in a human tissue, such as blood glucose level, by the method of this invention.

In one aspect, this invention provides a method for determining a disease state of a subject. The method comprises the steps of:
  (a) measuring at least one optical property at a first area on a human tissue to obtain a first set of data, the first area being subjected to a first temperature program;
  (b) measuring at least one optical property at a second area on the human tissue to obtain a second set of data, the second area being subjected to a second temperature program, the second temperature program being different from the first temperature program, the second area being morphologically similar to but not substantially overlapping with the first area;
  (c) inserting the first set of data and the second set of data into a mathematical relationship to calculate a mathematical output; and
  (d) comparing the mathematical output to a category selector to determine the disease state of the human.

The mathematical relationship is typically established by correlating the parameter with the disease state, which is determined by invasive methods. As used herein, the expression "disease state" means the status of a subject having an abnormal cardiovascular condition, a neoplasmic condition, or other disease that affects the tissues. A representative example of a disease state is diabetes. The thus-established mathematical relationship can be used to determine the disease state of a subject.

In another aspect, this invention provides a method for determining the concentration of an analyte in a tissue of a subject. The method comprises the steps of:
  (a) measuring at least one optical property at a first area on the tissue to obtain a first set of data, the first area being subjected to a first temperature program;
  (b) measuring at least one optical property at a second area on the tissue to obtain a second set of data, the second area being subjected to a second temperature program, the second temperature program being different from the first temperature program, the second area being morphologically similar to but not substantially overlapping with the first area; and
  (c) inserting the first set of data and the second set of data into a mathematical relationship to calculate the concentration of the analyte.

The mathematical relationship is typically established by correlating the parameter with the concentration of the analyte, which is determined by invasive methods. The thus-established mathematical relationship can be used to determine the concentration of the analyte in the tissue of a subject.

In another aspect, this invention provides an apparatus for carrying out the method of this invention. The apparatus comprises:
  (a) means for illuminating at least two areas of tissue with light;
  (b) means for collecting light re-emitted from the at least two areas of tissue;
  (c) means for measuring the intensity of the re-emitted light collected at the two areas of tissue; and
  (d) means for controlling the temperature of the at least two areas of the tissue simultaneously by means of temperature programs.

One embodiment of this invention involves a method for non-invasive diagnosis of a disease state, such as, for example, diabetes, or the concentration of an analyte, such as, for example, blood glucose level.

The measurements at the first area and at the second area can be made simultaneously. Alternatively, the measurements at the first area and at the second area can be made sequentially.

DETAILED DESCRIPTION OF THE INVENTION

As used herein, the expression "optical properties" refers to the absorption, scattering, emission, reflectance, and depolarization properties of biological tissues. The expression "optical parameter" refers to a parameter that describes and defines an optical property of a medium and its components. Examples of optical parameters include, but are not limited to, absorption coefficient, scattering coefficient, and extinction coefficient of analytes. The expression "scattering media" refers to media that both scatter light and absorb light. The expression "absorption coefficient" (i.e. $\mu_a$) refers to the probability of light absorption per unit path length, which is equal to 2.303 $\epsilon$C in cm$^{-1}$, where, $\epsilon$ is molar extinction coefficient and C is the molar concentration. The expression "reduced scattering coefficient" (i.e. $\mu_s'$) refers to the probability of equivalently isotropic (uniform in all directions) scattering per unit path length, which is equal to $\sigma\rho$ in cm$^{-1}$, where, $\sigma$ is scattering cross section and $\rho$ is the number density of scattering centers. The expression "light penetration depth" (i.e. $\delta$) refers to the rate of decay of intensity of light in scattering media with respect to the path traveled by the light in the same direction as the incident light. Light penetration depth represents the depth at which light intensity in the tissue is attenuated to 1/e of its original value and is related to the absorption and scattering coefficients as $\delta = 1/\sqrt{(3\mu_a(\mu_a+\mu_s'))}$.

The expression "diffuse reflectance" (reflectance therein unless specified otherwise) refers to measurement of light that is re-emitted from a sample at all angles different from the direction of the incident light, and over an area wider than the area where the incident light is introduced into the sample. The expressions "spatially resolved scattering" or "spatially resolved diffuse reflectance" and "localized reflection" refer to a measurement of light that is re-emitted from a sample and collected at several light collection sites at specific distances from a light introduction site. Alternatively, these expressions can refer to the light collected at a given light collection site on the sample boundary as a result of introducing light at discrete light introduction sites located on the same boundary at a set of defined distances from the light collection site. In both instances, $\mu_a$ and $\mu_s'$ are calculated from the intensity distribution of the re-emitted light with respect to distances, i.e., the re-emitted light intensity at a multiplicity of sampling distances. The expressions "re-emitted light" and "reflected light" are used synonymously herein, as are the expressions "reflectance" and the "intensity of re-emitted light", unless otherwise indicated.

The expression "light introduction site" means a location on the surface of a sample, e.g., a body part, tissue, or the like, at which light is injected or introduced into the sample, by means of, for example, an optical fiber. The source of the light can be located at the light introduction site or can be located remote from the light introduction site. If the source of light is located remote from the light introduction site, the light must be transmitted to the light introduction site by light transmitting means, such as, for example, optical fibers. The expression "light collection site" means a location on the surface of a sample, e.g., a body part, tissue, or the like, at which light that is re-emitted from the sample is collected for measurement. The detector, which determines the intensity of the re-emitted light, can be located at the light collection site or can be located remote from the light collection site. If the detector is located remote from the light collection site, the light must be transmitted to the detector by light transmitting means, such as, for example, optical fibers. The distance between a light introduction site and a light collection site, as measured along the surface of a sample, is defined as the "sampling distance". For a given sample, the sampling distance determines the mean distance from the surface of the sample into the interior of the sample at which the scattering and absorption events contribute to the measured re-emitted light. Such mean distance is hereinafter referred to as the "sampling depth", which is a function of the sampling distance. In this invention an "area on the surface of the tissue" may have multiple light introduction sites, multiple light collection sites, at least one sampling distance and at least one sampling depth and its optical properties are affected an independently-run temperature program. The expression "temperature program" refers to a sequence of temperature levels as a function of time. Examples of temperature programs include, but are not limited to, (1) maintaining a constant temperature over a period of time; (2) decreasing temperature over a period of time; (3) increasing temperature over a period of time; and (4) combinations of (1), (2), and (3). The expression "not substantially overlapping" means that the areas subjected to temperature programs can overlap slightly so long as the temperature programs to which the areas are subjected are distinguishable. However, it is preferred that the areas that are subjected to the temperature programs not overlap.

The expression "blood flow" means the velocity of red blood cells in blood vessels. Blood flow is usually measured by laser Doppler flowmetry. The term "vasodilatation" refers to the increase in diameter of a blood or lymph vessel by the action of a nerve. A chemical agent such as insulin or increasing tissue temperature can induce vasodilatation. The term "microcirculation" refers to the movement of blood in capillaries, arterioles, and venules as a result of constriction and relaxation of vessel walls. The term "artery" means a blood vessel that conducts blood from the heart to tissues and organs. Arteries are lined up with smooth flat cells (endothelium) and are surrounded by thick muscular elastic walls containing fibrous tissue. Arteries branch repeatedly until their diameter is less than 300 microns; these small-branched arteries are called "arterioles." Walls of arterioles are formed from smooth muscle. The function of arterioles is to control blood supply to the capillaries. The term "capillary" refers to a minute hair-like tube (5–20 microns in diameter) having a wall consisting of a single layer of flattened cells (endothelium). Capillary walls are permeable to water, oxygen, glucose, amino acids, carbon dioxide and inorganic ions. The capillaries form a network in all tissues. They are supplied by oxygenated blood by the arterioles and pass deoxygenated blood to the venules.

A "vein" is a blood vessel that conducts blood from the tissues and organs back to the heart; the vein is lined with smooth flat cells (endothelium) and is surrounded by muscular and fibrous tissue. Walls of veins are thin and the diameter of veins is large compared with the diameter of arteries. The vein contains valves that allow unidirectional flow of blood to the heart. A "venule" is a small vein that collects blood from capillaries and joins other venules to form a vein. A venule has more connective tissue than a capillary, but has similar small molecules permeability as a capillary. Arterioles and venules are connected through the capillary loop or through shunts. The term "shunt" refers to a passage or a connection (anastomosis) between two blood vessels. An arteriovenous shunt is a passage of blood from an artery (or arteriole) to a vein (or venule) that does not go through the capillary loop. The term "plexus" refers to a braid of blood vessels. In the skin, the "upper plexus" or the "superficial plexus" refers to the braid of arterioles and venules found at the top layer of the dermis. The "lower plexus" or deep plexus" refers to the braid of arterioles and venules that found at the lower layer of the dermis. Each of the braids is referred to as a "vascular plexus" and both are interconnected. Arterioles, venules, capillary loops, the upper plexus and the lower plexus comprise the microvasulature system and are responsible for controlling skin temperature and the flow of blood and nutrients to the skin and disposal of metabolic products from the skin.

Figure 1:
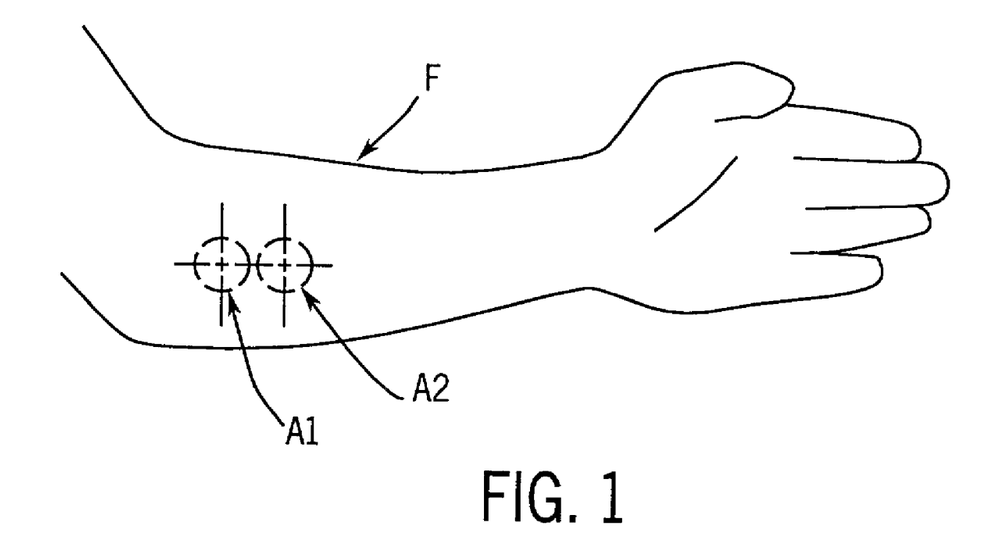
FIG. 1 Illustrates measurement areas on a human forearm.

FIG. 1 shows a human forearm "F", on which are marked of two morphologically similar, substantially non-overlapping areas "A1" and "A2" on the surface of the tissue. The two areas are selected to have similar morphology (such as the presence of hair, bone, appearance of veins). While not required, it is preferred that the areas be adjacent. Each area is subjected to a temperature program to induce optical changes, which result from changes in absorption and scattering properties of the tissue. The temperature programs are not identical. Changes in absorption properties of the tissue can be induced by changes in microcirculation, while changes in scattering properties of the tissue can be induced by changes in the refractive index mismatch between the scattering centers in the tissue and the fluid medium surrounding these centers. This mismatch is caused by changes in temperature.

Figure 2:
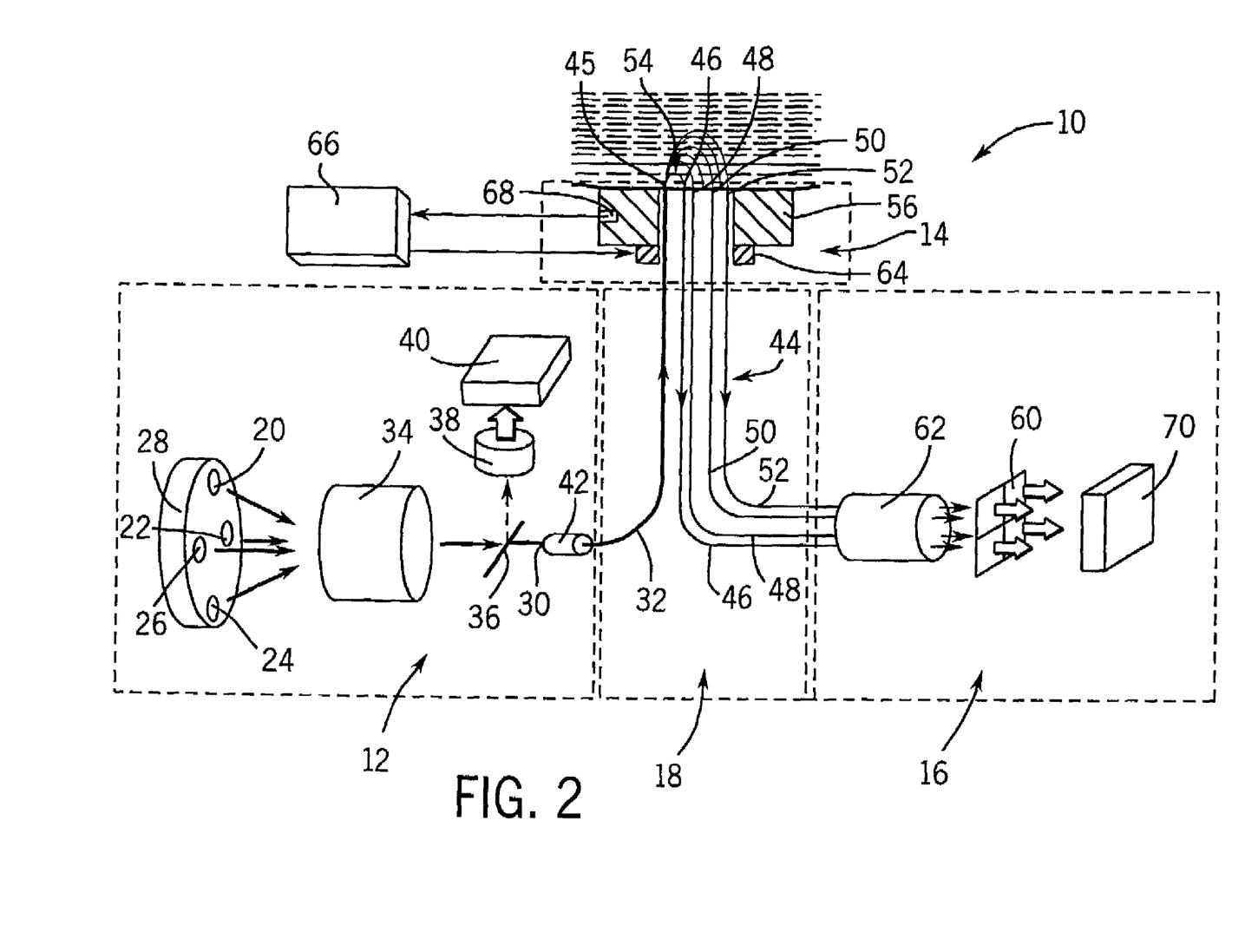
FIG. 2 is a schematic diagram illustrating a device suitable for use in this invention. The device employs one optical head and is suitable for sequential measurements. The portion of the device that contacts a body part is shown as a cross-section.

FIG. 2 illustrates an embodiment of a device suitable for use in this invention. This device can be used to subject two morphologically similar, non-overlapping areas on the surface of human skin to different temperature programs while optical measurements are made at these two morphologically similar, non-overlapping area on the surface of human skin. The device is similar to that described in WO 99/59464, which is incorporated herein by reference. As shown schematically in FIG. 2, the device 10 comprises a light source module 12, a human interface module 14, and a signal detection module 16. The human interface module 14 has a single optical head. As will be described later, different embodiments may have a plurality of optical heads. These three modules are interconnected through a branched optical fiber bundle 18. The light source module 12 comprises four light emitting diodes (LED's) 20, 22, 24, and 26, by means of which the output of light can be modulated. The LED's are mounted in a circular holder 28 and the light from the LED's is collected and then transferred onto an end 30 of an illuminating element 32 by means of a lens assembly 34, e.g., a 28 mm focal length RKE precision eyepiece (Edmund Scientific part No 30787). Each LED is modulated at a different frequency. A portion of the light is diverted by a beam splitter 36 and focused onto a silicon photodiode 38 (Model S-2386-44K 6C, Hamamatsu, Hamamatsu City, Japan) and a pre-amplifier 40 to generate a reference signal, which is used to correct for fluctuations in intensity of the source of light. The remainder of the light beam continues onto the end 30 of the illuminating element 32 housed at the source tip 42 of a fiber bundle 44.

An end 45 of the illuminating element 32 and the ends of the light collecting elements 46, 48, 50, and 52 are mounted in a common tip 54, which is situated at the center of a temperature-controlled disc 56 (2-cm diameter). The common tip 54 and the temperature-controlled disc 56 are parts of the human interface module 14. All of the elements 32, 46, 48, 50, and 52 are fibers made of low OH silica, and each has a diameter of 400 μm (Fiberguide Industries, Stirling, N.J.). The light re-emitted from the skin is collected by the light collecting elements 46, 48, 50, and 52 and transmitted to the signal detection module 16. A detector 60, e.g., a quadrant silicon photodiode detector (Advanced Photonics, P/N SD225-2321-040), located in the signal detection module 16 measures the intensity of light transmitted from the four light collecting elements 46, 48, 50, and 52. The distal end of each light collecting element is located in a detection tip 62.

The body interface module 14 of the device 10 can be mounted on a cradle (not shown) that is, in turn, mounted on an arm of a standard clinical reclining chair (not shown). The subject sits in the chair so that the forearm of the subject rests on the cradle. The optical head of the device, which is located in the body interface module 14, is pressed against the dorsal side of the subject's forearm at a constant force of, for example, 160 grams (approximately 45 grams per cm$^2$). Other means of placing the forearm of the subject in contact with the optical head of the device can also be used. A thermoelectric cooling/heating element 64 (Model SP1507-01AC, Marlow Industries, Dallas, Tex.) and a controller/power supply unit 66 (Marlow Industries, SE5000-02) controls the temperature of the disc 56, which is placed in contact with the skin of the forearm. A thermocouple (or thermistor) 68 has the function of sensing the temperature in the aluminum disc 56 and providing a feedback to the temperature controller 66. A personal computer employing LabView™ (version 5.1, National Instruments, Austin, Tex.) software program sets the temperature of the disc 56 by means of the controller 66. The personal computer and its accompanying software also manage the acquisition of data.

Light from the illuminating element 32 enters the skin through a body interface module 58 attached on the arm of the reclining clinical chair. The signals from four of the light collecting elements 46, 48, 50, and 52 are transmitted to the detector 60 (Advanced Photonics, P/N SD225-2321-040), one signal to each quadrant of the detector 60. The signal from each quadrant of the detector 60 is amplified separately by an amplifier 70 and measured by means of a multimeter (Model No. 3458A, Hewlett-Packard, Palo Alto, Calif.). The optical signals are collected and integrated every 30 seconds, because of the limitations of the data transfer rate between the multimeter and the personal computer.

A calibration algorithm is used to correct for fluctuation in the intensity and spectral output of the LED's, spectral response of the detector, relative light throughput of the illuminating element and each light collecting element, and dark current of the detection system (i.e., the current of the detection system when the light source is turned off). Accordingly, the magnitude of the reflectance signal thus obtained differs from its true value only by a common multiplicative factor that is unique for each set of elements, detector, and type of lamp.

The device in FIG. 2 has a single optical head; the device is capable of providing a defined temperature program while optical measurements are being made. In order to carry out the method of this invention, the optical head of the device is brought in contact with the tissue (e.g., human skin) at a first area thereof. A first defined temperature program is run while optical measurements are being made. The arm is moved to allow the device to contact the second area of the tissue, whereat a second defined temperature program is run while optical measurements are being made. In other words, the two areas are contacted sequentially, and the two optical measurements are made sequentially.

Figure 3:
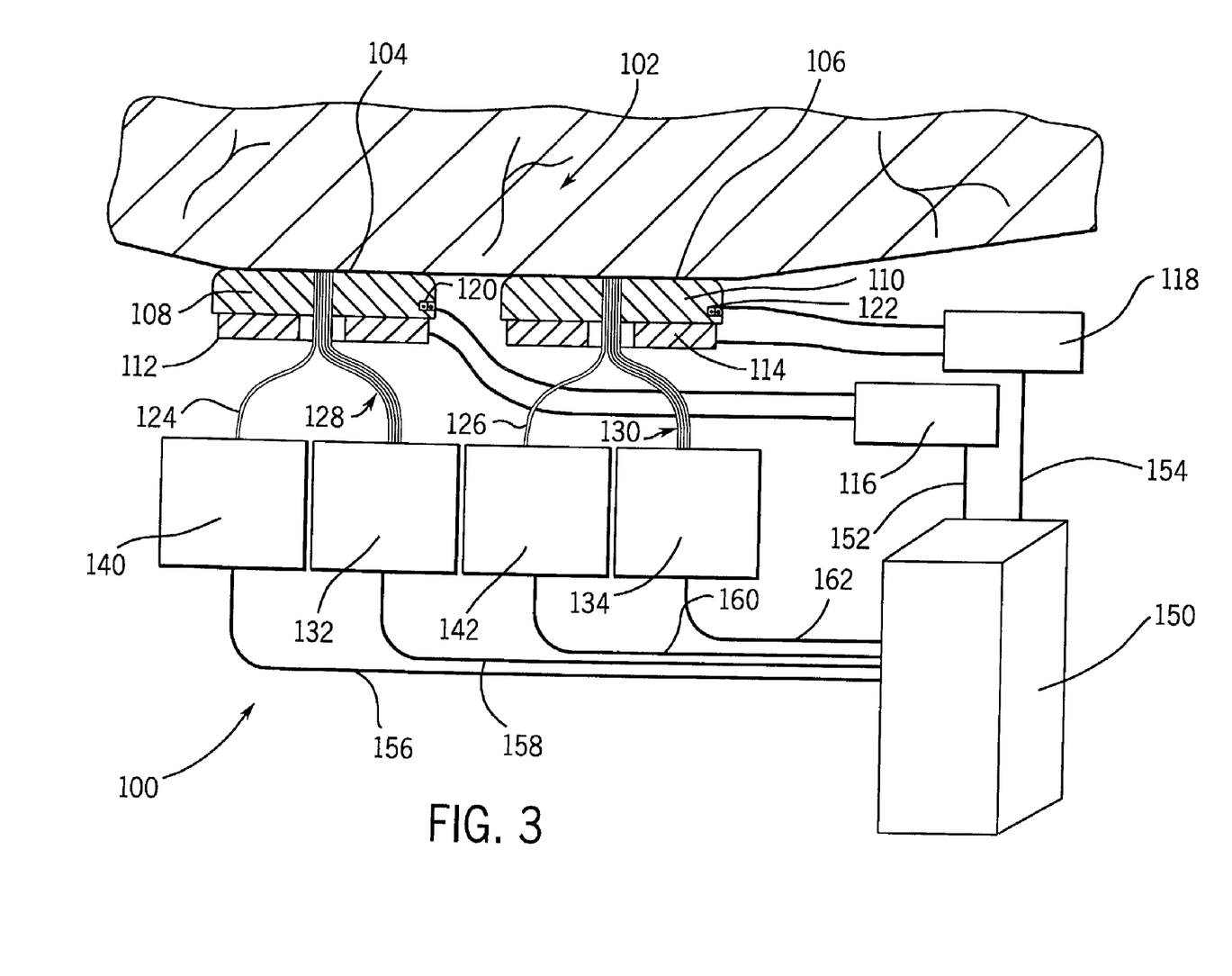
FIG. 3 is a schematic diagram illustrating a device suitable for use in this invention. The device employs two optical heads and is suitable for simultaneous measurements. The portion of the device that contacts a body part is shown as a cross-section.

FIG. 3 illustrates a device having two optical heads, each optical head capable of providing a defined temperature program while optical measurements are being made. The two optical heads of the device are mounted on a common bracket (not shown). The two optical heads are applied to the skin of the forearm of the subject in the same way as is the device having the single optical head described previously. A constant force spring is used to maintain the optical heads in contact with the forearm. The spring force applied is typically about 200 grams, although the precise amount of force is not critical to the operation of the invention.

Referring now to FIG. 3, a device 100 can be brought into contact with a body part 102 at two test areas 104, 106 on the body part 102. The device comprises two optical heads, which in turn comprise aluminum discs 108, 110, the temperatures of which can be controlled, and thermoelectric cooling/heating elements 112, 114. The temperature of each disc 108, 110 at each head is controlled by thermoelectric cooling/heating elements 112, 114. The thermoelectric cooling/heating elements 112, 114 (Model SP1507-01AC, Marlow Industries, Dallas, Tex.) and controller/power supply units 116, 118 (Marlow Industries, SE5000-02) control the temperature of the discs 108, 110, which are placed in contact with the skin, through power inputs from temperature controllers 116, 118. A thermocouple (or thermistor) 120, 122 has the function of sensing the temperature in each aluminum disc 108, 110 and providing a feedback to the temperature controller associated with the particular disc.

The optical heads also include illuminating fibers 124, 126. Light emitted from the skin is collected by fiber groups 128, 130 and fed into detector 132, which also contains electronics to amplify the signal collected from the first area, and detector 134, which also contains electronics to amplify the signal collected from the second area. Light source electronics 140 provide power to operate the light sources of the optical head that is in contact with the first area. In the same manner, light source electronics 142 provide power to operate the light sources of the optical head that is in contact with the second area. A microprocessor/computer 150 controls the temperature controllers 116, 118, light source electronics 140, 142, and signal amplification electronics 132, 134 through cables/connectors 152, 154, 156, 158, 160, and 162. When this device is brought in contact with the tissue, the two optical heads contact the tissue at the two areas simultaneously. The two temperature programs and the measurements accompanying them can be run simultaneously.

Thus, the method of this invention can be characterized as a method in which optical signals are collected at two morphologically similar, non-overlapping, preferably adjacent, areas as the temperature in each area is being maintained or modulated according to a temperature program. The measured values derived from the optical signals obtained are inserted into an algorithm that can be used for predicting a disease state (such as the diabetes mellitus disease state) or into an algorithm that can be used for determining the concentration of a substance in the body, such as blood glucose level.

When the optical measuring device is brought in contact with the skin or another tissue, several phenomena are observed with respect to the optical signal. In the case of skin, we have discovered that when light is introduced into the skin by an optical measuring device in contact with the skin and the intensity of light transmitted or reflected from the skin is measured, the optical signal measured follows a definite course over time. First, a sharp change in signal is observed over a time period of from about 1 to about 30 seconds. This change is manifested as a decrease in reflectance as a function of time. This decrease is the largest component of the signal change. The magnitude of the decrease varies with the geometry of the optical measuring device, the pressure imparted on the skin, and the nature of the skin of the individual. The change in optical signal as a function of time can be attributed to conformance of the skin, especially the stratum corneum, to the shape of the measuring device.

Second, a decrease in the intensity of reflected light or scattered light appears as a function of time. This decrease takes place over a longer time period, extending over minutes, and exhibits a more gradual slope than does the initial decrease. An increase in glucose concentration in the skin leads to a decrease in the reflected signal in a scattering measurement. An increase in glucose concentration also leads to a decrease in the scattering coefficient of skin. The change in the scattering coefficient is estimated to be $1 \times 10^{-4}$ per mM of glucose. The change in optical signal due to the initial interaction of the device or the mechanical compression of tissue is in the same direction as the effect of increasing glucose concentration, but is at least ten times greater than the increase that can be attributed to a change in glucose concentration.

Third, the difference between the temperature of the measuring device and the temperature of the skin causes a drift in the optical signal over time. If the measuring device is at a temperature higher than that of the skin, heat will flow from the device to the skin, thereby leading to an increase in temperature of the skin and, hence, an increase in scattering coefficient and the intensity of reflected light, as described in U.S. Ser. No. 09/419,461, filed Oct. 15, 1999. On the other hand, if the measuring device is at a temperature lower than that of the skin, heat will flow from the skin to the device. This flow of heat will lead to a temporary decrease in the temperature of the skin, a decrease in the scattering coefficient, and a concomitant decrease in intensity of reflected light.

Finally, changes in the surface and subsurface structure of the tissue as a function of time will also affect the optical signal. Thus, opening and closing of arterio-venous shunts, movement of interstitial fluid, etc., will lead to a slow change in the measured optical signal.

The method of this invention provides optical measurements along with controlled temperature changes of the cutaneous vascular bed, thereby allowing tracking of microvascular defects and cutaneous structural differences. This tracking is achieved without inconvenience to the subject, such as may be encountered in contralateral cooling of the arm or heating to 44° C., as in capillary video microscopy. The method of this invention can also eliminate the need for physical movement, such as sitting and standing, during the measurement.

The two-area measurement accompanied by temperature programming corrects for the spontaneous change in optical signal (drift) resulting from the interaction between the probe and skin, during the measurement.

The optical measurements required in this invention can be measurements of diffuse reflectance or spatially resolved diffuse reflectance. Transmission measurements can be used with the method of this invention, when the optical device is applied to a thin body part where temperature can be controlled and varied over the volume interrogated by the light beam. The ear lobe or the webs between the fingers are potential sites for transmission measurements.

One aspect of this invention is the determination of the disease state, e.g., diabetic status, of a subject. A mathematical function can be derived from optical signals at two areas of the tissue (e.g., skin), wherein the temperature is controlled at each area by means of temperature programs. A temperature program can specify a constant temperature value, a set of decreasing temperature values, a set of increasing temperature values, or a set of temperature values that increase and decrease over the given period of time. One such function is expressed by Equation (2) as:

$$f(R_{A1T1}, R_{A1T2}, R_{A2T3}, R_{A2T4}) = [Ln\ (R_{A1T1}/R_{A1T2})] - [Ln\ (R_{A2T3}R_{A2T4})] \quad (2)$$

where $R_{A1T1}$ represents the measured light intensity at temperature $T_1$ at the first area of skin, $R_{A1T2}$ represents the measured light intensity at temperature $T_2$ at the same first area of the skin, $R_{A2T3}$ represents the measured light intensity at temperature $T_3$ at a second area of the skin, and $R_{A2T4}$ represents the measured light intensity at temperature $T_4$ at the same second area of the skin.

$T_1$ and $T_2$ represent the limits of the first temperature program. $T_3$ and $T_4$ represent the limits of the second temperature program. The temperature program in the first area should differ from the temperature program in the second area. Otherwise, the measurements are merely repetitive.

The derived function(s) $f(R_{A1T1}, R_{A1T2}, R_{A2T3}, R_{A2T4})$, determined at a plurality of sampling distances and at a plurality of wavelengths, and the known disease states, e.g., diabetic or non-diabetic, of each of a set of subjects (i.e., the calibration set) can be processed to generate a discriminant function D. Discriminant functions are used in the art of pattern recognition. See for example Duda and Hart, *Pattern Classification and Scene Analysis*, John Wiley & Sons (1973), pages 17 to 20, and pages 130 to 138, which pages are incorporated herein by reference. The discriminant function is a decision rule for categorizing objects, in this case placing diabetic subjects and non-diabetic subjects in their respective categories. A subject is classified as diabetic if D>0, and non-diabetic if D<0. As used herein, the decision rule for categorizing objects has been referred to as a "category selector."

The true disease state must, of course, be known in order to utilize optical measurements for the calibration set. D is typically a quadratic expression comprising a plurality of the functions of the type $f(R_{A1T1}, R_{A1T2}, R_{A2T3}, R_{A2T4})$.

An example of a discriminant function is a quadratic expression of the form $$D = \sum_i \sum_j a_{ij}(\delta_i f_i)(\delta_j f_j) + \sum_i a_i \delta_i f_i + a_o \text{ where} \quad (3)$$

$$\delta_i = 1 \text{ or } 0; \text{ and } \sum_i \delta_i = K \quad (4a)$$

$$\delta_j = 1 \text{ or } 0; \text{ and } \sum_j \delta_j = K \quad (4b)$$

$a_{ij}$, $a_i$, and $a_o$ are constants determined from the calibration set, and subscripts i or j are indices to specific combinations of wavelength and sampling distance. The number K limits the total number of individual wavelength-sampling distance combinations used in the discriminant function. Those skilled in the art can derive and use discriminant functions of other forms, or use neural networks to achieve similar classifications. Those skilled in the art will recognize that the two-category classification mentioned above is merely a special case of a multi-category classification and that discriminant functions for multi-category situations can be generated.

The diabetic status of a subject is represented by $S_i$ where $S_i = +1$ for a diabetic subject $S_i = -1$ for a non-diabetic subject The value of the function D can be calculated for each subject i and expressed as $D_i$. If $D_i$ and $S_i$ have the same sign, the subject is categorized as concordant (i.e., the subject is classified properly). If $D_i$ and $S_i$ have different signs, the subject is categorized as discordant (i.e., the subject is classified improperly). The number of subjects in each category (concordant or discordant) is determined.

The coefficients of the quadratic function D of the calibration (training) set are used to calculate the value of the function $D_i$ for the prediction set. If the calculated value of $D_i$ for a given subject in the prediction set is positive ($D_i > 0$), the subject is classified as diabetic. If the calculated value of $D_i$ for a given subject in the prediction set is negative ($D_i < 0$), the subject is classified as non-diabetic. A 2×2 prediction matrix of the type shown in Table 1 is then established for each experimental condition examined (e.g., initial temperature, final temperature, and cooling rate) at each area. The number of true diabetic subjects identified as diabetic is designated "a", the number of true non-diabetic subjects identified as non-diabetic is designated "d", the number of diabetic subjects identified as non-diabetic (false negative) is designated "c", and the number of non-diabetic designated as diabetic (false positive classification) is designated "b". The number of concordant subjects (a and d) are placed along a diagonal that represents the concordant diabetics and non-diabetics. The numbers of discordant subjects (b and c) are placed on the other diagonal, as indicated in Table 1. The above-described classification method can be used for screening for diabetes in human subjects.

TABLE 1

| | True Status | |
|---|---|---|
| Optical Test Result | Diabetic | Non-diabetic |
| Diabetic | a | b |
| Non-diabetic | c | d |

The quality of the differentiation between diabetic and non-diabetic subjects is judged by sensitivity, specificity, positive predictive value (PPV), and negative predicted value (NPV). The term "sensitivity" refers to the ability of a test to identify individuals who are truly positive. The measure of sensitivity is ratio of the number of subjects identified as positive by the test method divided by the total number of truly positive samples as determined by the reference method (i.e., the true status). The term "specificity" refers to the ability of a test to identify individuals who are truly negative. The measure of specificity is the ratio of the number of subjects identified as negative by the test method divided by the total number of truly negative subjects as determined by the reference method. The expression "positive predictive value" or "PPV" is the probability of being truly positive given a positive test result. It is the ratio of the number of truly positive subjects identified as positive by the test method divided by the total number of positive subjects as determined by the test method (in this invention, an optical method). The expression "negative predictive value" or "NPV" is the probability of being truly negative given a negative test result. It is the ratio of the number of truly negative subjects identified by the test method divided by the total number of negative subjects as determined by the test method. The expression "p value" is a parameter that refers to the ability to separate two partially overlapping populations using the $\chi^2$ test. The smaller the value of p, the better is the separation between the two populations.

The performance parameters of the method, namely, sensitivity, specificity, positive predictive value (PPV), and negative predictive value (NPV) are calculated from the population number a, b, c, and d, where Sensitivity=$a/(a+c)$, Specificity=$d/(d+b)$ Positive predictive value (PPV)=$a/(a+b)$, and Negative predictive value (NPV)=$d/(c+d)$.

Another suitable application for the method of this invention is a method for the non-invasive determination of the concentration of an analyte, e.g., glucose, in human tissue. The method involves contacting the skin with an optical head at two areas, the areas being morphologically similar but non-overlapping, the areas being subject to different temperature programs.

A linear regression relationship utilizing, for example, differences of optical measurements at the two areas can be derived for each subject to generate a calibration relationship that relates the concentration of glucose in tissue and the optical signals observed at the first and second areas while these areas are subject to different temperature programs. The concentration of an analyte, e.g., glucose, can be determined from an equation such as the following:

$$[G] = b_0 + \sum_i \sum_j c_{ij}[\ln(R(\lambda_i, r_j, t_1, A_1)) - \ln(R(\lambda_i, r_j, t_1, A_2))] + \sum_i \sum_j d_{ij}[\ln(R(\lambda_i, r_j, t_2, A_1)) - \ln(R(\lambda_i, r_j, t_2, A_2))] \quad (5)$$

where [G] represents the concentration of analyte (e.g., glucose); $R(\lambda_i, r_j, t_1, A_1)$ represents the quantity of reflected light at $\lambda_i$, $r_j$, $t_1$, $A_1$; $R(\lambda_i, r_j, t_1, A_2)$ represents the quantity of reflected light at $\lambda_i$, $r_j$, $t_1$, $A_2$; $R(\lambda_i, r_j, t_2, A_1)$ represents the quantity of reflected light at $\lambda_i$, $r_j$, $t_2$, $A_1$; $R(\lambda_i, r_j, t_2, A_2)$ represents the quanity of reflected light at $\lambda_i$, $r_j$, $t_2$, $A_2$; $\lambda_i$ represents the wavelength of light; $r_j$ represents the sampling distance; $t_1$ represents a first point in time from the time of contact of the optical device with the tissue, e.g., skin; $t_2$ represents a second point in time from the time of contact of the optical device with the tissue, e.g., skin; $A_1$ refers to the first area; and $A_2$ refers to the second area. The quantities $b_0$, $c_{ij}$, $d_{ij}$ are constant coefficients that are determined by means of calibration.

Because the temperature program and the time elapsing between applying the optical head to the tissue determines the subcutaneous temperature, Equation (5) is actually an expression of the value of concentration of the analyte as a function of temperature at each measurement area as shown by equation (6):

$$[G] = b_0 + \sum_i \sum_j c_{ij}[\ln(R(\lambda_i, r_j, t_1, A_1)) - \ln(R(\lambda_i, r_j, t_2, A_2))] + \sum_i \sum_j d_{ij}[\ln(R(\lambda_i, r_j, t_3, A_1)) - \ln(R(\lambda_i, r_j, t_4, A_2))]$$

where [G] represents the concentration of analyte (e.g., glucose); $R(\lambda_i, r_j, T_1, A_1)$ represents the quantity of reflected light at $\lambda_i$, $r_j$, $T_1$, $A_1$; $R(\lambda_i, r_j, T_2, A_2)$ represents the quantity of reflected light at $\lambda_i$, $r_j$, $T_2$, $A_2$; $R(\lambda_i, r_j, T_3, A_1)$ represents the quantity of reflected light at $\lambda_i$, $r_j$, $T_3$, $A_1$; $R(\lambda_i, r_j, T_4, A_2)$ represents the quantity of reflected light at $\lambda_i$, $r_j$, $T_4$, $A_2$; $\lambda_i$ represents the wavelength of light; $r_j$ represents the sampling distance; $T_1$ represents the temperature at the first area at time $t_1$, $T_2$ represents the temperature in the first area at time $t_2$, $T_3$ represents the temperature in the second area at time $t_1$, and $T_4$ represents the temperature in the second area at time $t_2$. Other examples of temperature programs can be developed by those skilled in the art and equations similar to equations (5) and (6) can be developed to express the concentration of an analyte without deviating from the scope and spirit of this invention. The temperature program applied to the first area must be different from the temperature program applied to the second area. The quantities $b_0$, $c_{ij}$, and $d_{ij}$ are constant coefficients that are determined by means of calibration.

The method of this invention can be used over a temperature range of from about 0° C. to about 45° C. A preferred temperature range is from about 10° C. to about 42° C., and a more preferred temperature range is from about 20° C. to about 40° C. Generally, the temperature range should be sufficient to provide a detectable change in light penetration depth in tissue without any temperature related injury to the tissue or any significant discomfort to the subject.

One of the embodiments of this invention includes both the temperature dependence of cutaneous circulation and the temperature dependence of structural parameters of the skin in the diagnosis of diabetes and diabetes complications. The measurement of optical properties of human skin across a boundary of the skin is adversely affected by the non-homogeneity of the different layers of the skin. Hormones, drugs, and metabolites in the blood in capillaries contribute to changes in the optical signals measured. The interaction of the optical measuring device and the skin may have different optical effects depending on the state of perfusion of the skin. Thus, highly perfused skin, with high blood content in the capillaries, will be affected by the interaction of the device with the skin and the temperature equilibration between the device and the skin in a different manner than will be a lightly perfused skin, with low blood content in the capillaries. These effects were not mentioned in the prior art. The various embodiments of this invention address these effects and compensate for their contribution to the optical signals. Such compensation will lead to better assessment of the diabetic status and determination of concentration of analytes, such as glucose, in human tissue, such as, for example, human skin.

Non-invasive optical measurements disclosed in the prior art involve illumination and collection of light at a single area on the surface of a body part. Several attempts at spatial averaging of signal over more than one measurement area are used for LDF and applied for the determination of bilirubin. In the case of spatial averaging, the measurement is repeated at several areas on the surface of the body part, the optical parameter is determined at each area, and an average value of the optical parameter is calculated. Alternatively, the signal can be measured at several areas on the surface of the body part, averaged, and the concentration of the analyte calculated from the mean of the individually measured signals. The use of a plurality of areas in effect averages out tissue heterogeneity and analyte distribution in tissue. However, in measurements in a plurality of areas, either the temperature is not controlled or the temperature is not varied according to a temperature program. An example of a device in the art that uses spatial averaging of the signal is the bilirubin measurement device having the trademark BiliCheck® and manufactured by SpectRx Inc, (Norcross, Ga.). Another commercially available device that uses spatial averaging is the Peri Flux 4041 measurement device, manufactured by Perimid AB (Jarfalla,Sweden). None of the devices in the prior art discloses the use of measurements of optical parameters under conditions of defined temperature programs at a plurality of detection areas.

The prior art is silent as to the effect of the interaction between the optical measuring device and the skin. The prior art is also silent as to the effect of the interaction between the test fixture or the body part holder and the body part on the measured optical signal, and hence on the value of concentration determined for the analyte.

This invention provides methods and devices for non-invasively measuring at least one clinical diagnostic parameter of a biological sample, such as, for example, a body part. The parameter can be selected, for example, from those such as the presence of a disease condition, progression of a disease state.

This invention addresses the deficiency in the prior art by providing a method to compensate for or alleviate the following effects:

(a) effect of the interaction between the optical measuring device and the tissue;

(b) effect of the interaction between the body part and the body part holder on the measured optical signal, i.e. mechanical compression of the tissue;

(c) effect of thermal equilibration between the body part and the measuring device on light propagation in skin and the measured optical signal; and (d) effect of surface and subsurface structural differences of the tissue on the measured optical signal.

U.S. Pat. Nos. 5,057,695; 5,551,422; 5,676,143; 5,492,118; 5,419,321; 5,632,273; 5,513,642; and 5,935,062 are silent as to measuring optical signals at more than one area on the skin, wherein temperature is varied independently at each area. Other methods known in the art operate on large body masses, such as the skull, thigh, or large arm muscles. The cutaneous volumes sampled in the methods in the prior art are too large to allow effective temperature control or effective temperature modulation over these large masses.

The method of this invention offers an advantage over laser Doppler flow measurements alone, because laser Doppler flow measurements deal with cutaneous blood flow in the upper 200 micrometers of the skin. Laser Doppler flow measurements do not account for any structural parameters or spectral effects, because laser Doppler flow measurements only measure the Doppler shift at a single wavelength.

Disease states that can be diagnosed using the method of this invention include, but are not limited to, diabetic status, peripheral vascular disease, a dermal disease state, or a neoplasmic disease state.

The method of this invention can be used on the surface of any tissue wherein light can be introduced into a tissue boundary and intensity of re-emitted light can be measured across the same or another tissue boundary, while at the same time temperature can be modulated to affect a change in light penetration depth in tissue. Accordingly, a temperature-controlled endoscopic probe can be used to diagnose lesions ulcers on the surface of the esophagus or the surface of the cervix.

EXAMPLES

The following non-limiting examples further illustrate the present invention.

Example 1

A device of the type shown in FIG. 2 was constructed. The device was capable of performing optical measurements at a single area on the surface of the skin at a given time. Thus, the device was required to be applied twice to the surface of the skin at two morphologically similar, adjacent, substantially non-overlapping areas on the skin.

The wavelengths of the LED's and the frequency at which each one was modulated are shown in Table 2.

TABLE 2

| LED Number | Wavelength (nm) | Modulation frequency (Hz) | Half band width (nm) |
| --- | --- | --- | --- |
| 1 | 660 | 1024 | 15 |
| 2 | 590 | 819 | 15 |
| 3 | 935 | 585 | 25 |
| 4 | 890 | 455 | 25 |

The distance from the center of each light collecting element 46, 48, 50, and 52 to the center of the illuminating element 32 defined the sampling distances $r_1$, $r_3$, $r_4$, and $r_6$ of this device, which are set forth in Table 3.

TABLE 3

| Element | $r_1$ | $r_3$ | $r_4$ | $r_6$ |
| --- | --- | --- | --- | --- |
| Sampling distance (mm) | 0.44 | 0.92 | 1.21 | 1.84 |

Example 2

The device described in Example 1 was used in this example. Programmed temperature changes and the optical measurements were carried out at each of the two areas on the surface of the forearm as illustrated in FIG. 1. The body interface module 14 of the device 10 was mounted on a cradle (not shown) that was, in turn, mounted on the left arm of a standard clinical reclining chair (not shown). The subject sat in the chair so that the forearm of the subject rested on the cradle. The head of the optical device, which is located in the body interface module 14, was pressed against the dorsal side of the subject's forearm and the data were collected from the time the head of the optical device contacted the skin. Data were collected at the two area sequentially while each area was subjected to a different temperature program. Data from the two areas were used to create a calibration relationship. At one area of the skin, the temperature was maintained at 34° C. for 30 seconds. The temperature was then lowered to 22° C. at the rate of 4° C. per minute. Optical readings were collected every five seconds for four minutes. A second area on the surface of the forearm was maintained at 34° C. for 4½ minutes. Optical readings were collected every five seconds for four minutes.

The optical data was divided into two classes—the class of diabetics and the class of non-diabetics. A 2×2 table that related the subject's disease status to the optical signal was constructed. The subject's disease status was determined by a reference method wherein the subject had previously been diagnosed as either diabetic or non-diabetic. Four diabetics and four non-diabetics were tested six times to generate 48 data points that were used to generate a calibration relationship. This calibration relationship was used to predict the diabetic status of subjects who were part of a new group, the prediction group. This group included six diabetics and six non-diabetics; each member of the prediction group was tested two times. Prediction of the diabetic status in 120 seconds is shown in Table 4.

TABLE 4

|  | True Status | |
| --- | --- | --- |
| Optical Test Result | Diabetic | Non-diabetic |
| Diabetic | 11 | 3 |
| Non-diabetic | 1 | 9 |

The quality of the differentiation between diabetic and non-diabetic subjects as judged by sensitivity, specificity, positive predictive value (PPV), and negative predicted value (NPV) at different combinations of temperatures is shown in Table 5.

TABLE 5

| Time | Temperature (° C.) | | p | Sensitivity | Specificity | PPV | NPV |
| --- | --- | --- | --- | --- | --- | --- | --- |
| (sec) | Area 1 | Area 2 | | | | | |
| 120 | 34 | 28 | 0.0038 | 92 | 75 | 79 | 90 |
| 150 | 34 | 26 | 0.0011 | 92 | 83 | 85 | 91 |
| 180 | 34 | 24 | 0.0007 | 100 | 75 | 80 | 100 |
| 210 | 34 | 22 | 0.0011 | 83 | 92 | 91 | 85 |

The temperature programs exemplified in Table 5 could be used to predict the diabetics with a sensitivity of 85% to 100% and specificity between 75% and 92% depending on the temperature differential between the two areas. The PPV was higher than 80% and the NPV was higher than 85%.

Example 3

The procedure described in Example 2 was repeated in this example. In this example, one area on the surface of the forearm was maintained at a temperature of 38° C. for 30 seconds. The temperature of this area was then lowered to a temperature of 22° C. at the rate of 5.33° C. per minute. Optical readings were collected every five seconds for four minutes. A second area on the surface of the forearm was maintained at a temperature of 22° C. for 30 seconds. The temperature of this area was then raised to 38° C. at the rate of 5.33° C. per minute. Optical readings were collected every five seconds for four minutes.

The optical data was divided into two classes—the class of diabetics and the class of non-diabetics. A 2×2 table that related the subject's disease status to the optical signal was constructed. The subject's disease status was determined by a reference method wherein the subject had previously been diagnosed as either diabetic or non-diabetic. Four diabetics and four non-diabetics were tested six times to generate 48 data points that were used to generate a calibration relationship. This calibration relationship was used to predict the diabetic status of subjects who were part of a new group, the prediction group. This group included six diabetics and six non-diabetics; each member of the prediction group was tested two times. Prediction of the diabetic status in 120 seconds is shown in Table 6.

TABLE 6

|  | True Status | |
| --- | --- | --- |
| Optical Test Result | Diabetic* | Non-diabetic* |
| Diabetic | 11 | 1 |
| Non-diabetic | 0 | 9 |

*Total number did not equal 12 because subjects displaying outlying signals were rejected.

Again, the quality of the differentiation between diabetic and non-diabetic subjects as judged by sensitivity, specificity, positive predictive value (PPV), and negative predicted value (NPV) was estimated at different combinations of temperatures at the two areas is shown in Table 7.

TABLE 7

| Time | Temperature (° C.) | | p | Sensitivity | Specificity | PPV | NPV |
| --- | --- | --- | --- | --- | --- | --- | --- |
| (sec) | Area 1 | Area 2 | | | | | |
| 120 | 30 | 30 | 0.0001 | 92 | 90 | 92 | 100 |
| 150 | 27.3 | 32.7 | 0.0016 | 73 | 100 | 100 | 77 |
| 180 | 24.7 | 35.3 | 0.0004 | 90 | 90 | 90 | 90 |
| 210 | 22 | 38 | 0.0004 | 82 | 92 | 100 | 83 |

The temperature programs in Table 7 could be used to predict the diabetics with a sensitivity of 73% to 92% and specificity between 90% and 100%, depending on the temperature differential between the two areas. The PPV was higher than 90% and the NPV was higher than 77%.

Example 4

The procedure described in Example 2 was repeated in this example. In this example, one area on the surface of the forearm was maintained at a temperature of 30° C. for 30 seconds. The temperature of this area was then lowered to 22° C. at the rate of 2.67° C. per minute. Optical readings were collected every five seconds for up to 4 minutes. A second area on the surface of the forearm was maintained at a temperature of 30° C. for 30 seconds. The temperature of this area was then raised to 38° C. at the rate of 2.67° C. per minute. Optical readings were collected every five seconds for up to 4 minutes.

The optical data was divided into two classes—the class of diabetics and the class of non-diabetics. A 2×2 table that related the subject's disease status to the optical signal was constructed. The subject's disease status was determined by a reference method wherein the subject had previously been diagnosed as either diabetic or non-diabetic. Four diabetics and four non-diabetics were tested six times to generate 48 data points that were used to generate a calibration relationship. This calibration relationship was used to predict the diabetic status of subjects who were part of a new group, the prediction group. This group included six diabetics and six non-diabetics; each member of the prediction group was tested two times. Prediction of the diabetic status in 120 seconds is shown in Table 8.

TABLE 8

| Optical Test Result | True Status | |
|---|---|---|
| | Diabetic | Non-diabetic |
| Diabetic | 10 | 0 |
| Non-diabetic | 2 | 12 |

The quality of the differentiation between diabetic and non-diabetic subjects as judged by sensitivity, specificity, positive predictive value (PPV), and negative predicted value (NPV) was estimated at different combinations of temperatures at the two areas. The results are shown in Table 9.

TABLE 9

| Time | Temperature (° C.) | | | | | | |
|---|---|---|---|---|---|---|---|
| (sec) | Area 1 | Area 2 | p | Sensitivity | Specificity | PPV | NPV |
| 120 | 26 | 34 | 0.0002 | 83 | 100 | 100 | 86 |
| 150 | 24.7 | 35.3 | 0.0011 | 92 | 83 | 85 | 91 |
| 180 | 23.3 | 36.7 | 0.0007 | 75 | 100 | 100 | 80 |
| 210 | 22 | 38 | 0.0002 | 100 | 83 | 86 | 100 |

The temperature programs in Table 9 could be used to predict the diabetics with a sensitivity of 75% to 100%, and specificity between 83% and 100% depending on the temperature differential between the two areas. The PPV was higher than 85% and the NPV was higher than 80%.

Example 5

Figure 4:
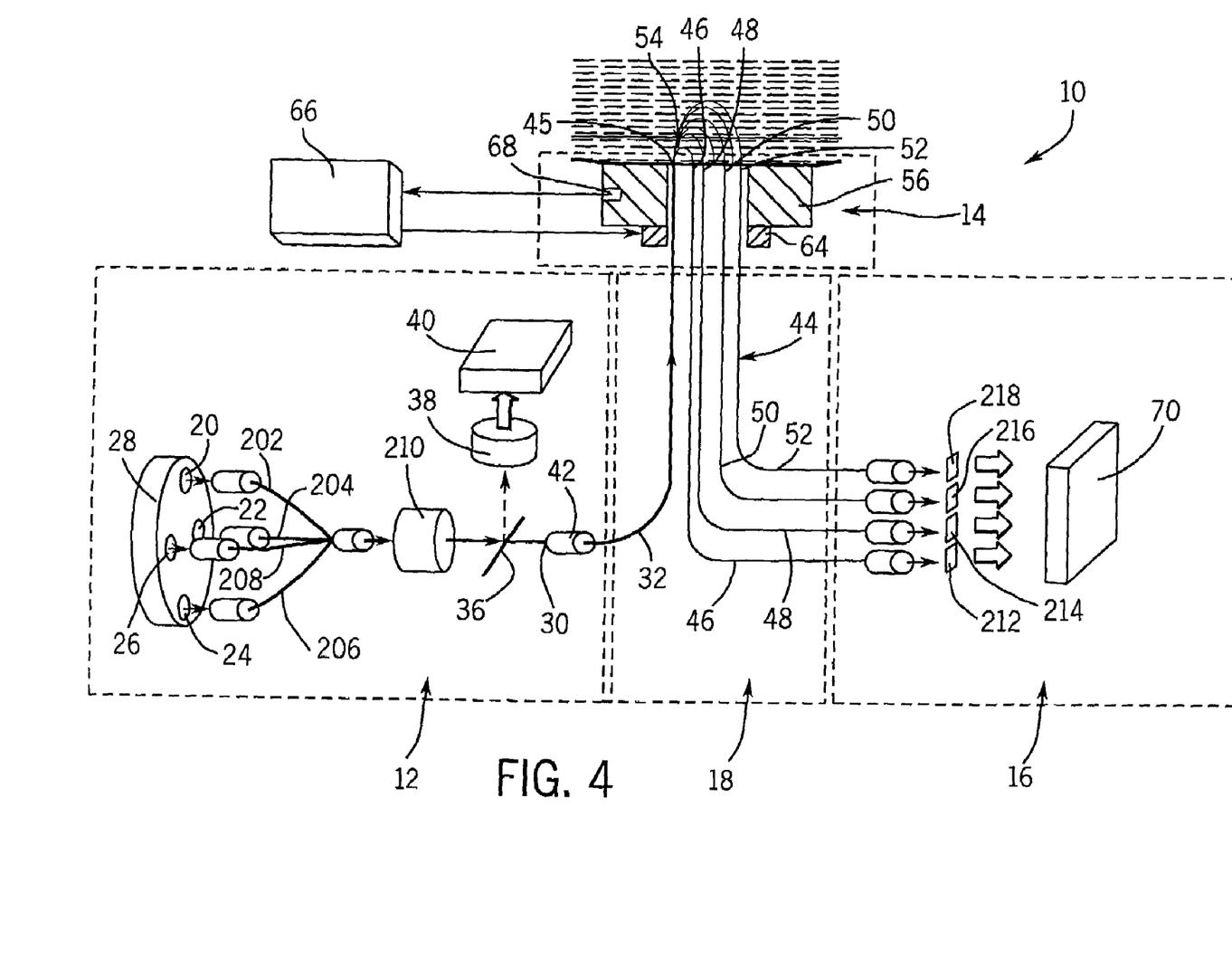
FIG. 4 is a schematic diagram illustrating a device suitable for use in this invention. The device employs one optical head and is suitable for sequential measurements. The portion of the device that contacts a body part is shown as a cross-section. The device of FIG. 4 is a variation of the device shown in FIG. 2.

A device similar to that described in Example 1 was used. This device is illustrated in FIG. 4. The device shown in FIG. 4 is similar to the device shown in FIG. 2, except for the following modifications. The lens assembly 34 (see FIG. 2) was replaced by a four-in-one fiber bundle 200 manufactured by Fiberguide Industries. The fiber bundle 200 contained four fibers designated by the reference numerals 202, 204, 206, 208. Each of the four fibers 202, 204, 206, 208 had a diameter of 400 micrometers and were made of the same material as the illuminating element 32 and the light collecting elements 46, 48, 50, and 52 described previously. Light from each of the LED's 20, 22, 24, and 26 was fed into each of four fibers 202, 204, 206, 208, respectively, the ends of which fibers were bundled in a ferrule (not shown), and focused at the beam splitter 36 leading to the illuminating element 32 by means of a group of lenses 210. Instead of a quadrant detector 60 (see FIG. 2), four individual photodiodes 212, 214, 216, and 218 were used to detect the light from the four fibers 46, 48, 50, and 52, respectively. The electronics and optics were packaged in an aluminum brief case, and the fiber bundle 44 was routed to the body interface module 14. In the device shown in FIG. 4, the reference numerals that matched those of FIG. 2 denote components that are identical or substantially identical to those components of FIG. 2 that employ the same reference numerals. The body interface module 14 was placed on a table (not shown). The subject sat in a chair in front of the body interface module 14 and the arm of the subject was placed on a cradle (not shown) that had been placed on the table. The subject sat in the chair so that the forearm of the subject rested on the cradle. The head of the optical device, which is located in the body interface module 14, was pressed against the dorsal side of the subject's forearm and the data were collected from the time the head of the optical device contacted the skin. The temperature program was the same as used in Example 4 (from 30° C. to 22° C. at the first area, and from 30° C. to 38° C. at the second area). Data were collected at the two areas sequentially for three minutes.

The test was run at a local hospital; a protocol approved by the hospital's Institutional Review Board was used. Subjects were admitted to the hospital the night before the test and were confined for two days. On each day, 10 non-invasive tests and 10 finger stick measurements, taken at the same time as the non-invasive measurements, were conducted. Subjects were fed a standard diet and used diabetes medications as prescribed by their physicians. Data from the two areas were used to create a calibration relationship. A leave-one-out cross validation method was used to estimate the standard error of prediction and the correlation coefficient.

A linear regression relationship utilizing differentials of optical measurements can be derived for each subject by means of Equations (5) and (6). In this example, the values of the measurements used were taken at 30 seconds and 180 seconds after the optical head initially contacted an area of the skin.

A summary of the data is shown in Table 10. In this table, the standard error of prediction, which is the root means square calculated prediction error using leave-one-out cross validation method, is "SEP". The leave-one-out cross validation method is described in Wu et al., "Noninvasive Determination of Hemoglobin and Hematocrit Using a Temperature-Controlled Localized Reflectance Tissue Photometer", Analytical Biochemistry, 2000;287:284–293, incorporated herein by reference. The cross validation prediction correlation coefficient is "r", and the standard deviation of the 20 invasively-determined glucose values over the two days is "SDP". The figure of merit is defined as the ratio of the correlation coefficient "r" to the value of (SEP/SDP). The higher the figure of merit, the better the correlation.

The value of (SEP/SDP) is a measure of the spread of the predicted blood glucose level relative to one standard deviation of the blood glucose level in the calibration set. A successful cross-validation requires that the ratio (SEP/SDP) be less than 1.0. In this example, the cut-off value for a successful cross-validation prediction of blood glucose level was set at a SEP/SDP ratio of 0.9. The values of SEP, r, and SEP/SDP are tabulated in Table 10. The underlined SEP/SDP values represent the successful predictions of blood glucose level.

TABLE 10

| Subject | SEP (mg/dL) | Correlation coefficient r | SDP (mg/dL) | SEP/SDP | Figure of merit |
|---|---|---|---|---|---|
| 1 | 78.0 | 0.63 | 99.2 | 0.79 | 0.80 |
| 2 | 57.3 | 0.53 | 66.6 | 0.86 | 0.62 |
| 3 | 44.5 | 0.66 | 59.6 | 0.75 | 0.88 |
| 4 | 52.6 | 0.25 | 53.6 | 0.98 | 0.25 |
| 5 | 39.7 | 0.62 | 50.6 | 0.78 | 0.79 |
| 6 | 50.6 | 0.65 | 66.1 | 0.77 | 0.85 |
| 7 | 41.7 | 0.74 | 63.0 | 0.66 | 1.12 |
| 8 | 31.0 | 0.71 | 44.3 | 0.70 | 1.01 |
| 9 | 38.5 | 0.80 | 64.4 | 0.60 | 1.33 |
| 10 | 51.7 | 0.38 | 54.3 | 0.95 | 0.40 |
| 11 | 38.8 | 0.49 | 44.0 | 0.88 | 0.55 |
| 12 | 40.5 | 0.83 | 74.2 | 0.55 | 1.52 |
| 13 | 63.7 | 0.52 | 71.5 | 0.89 | 0.59 |
| 14 | 109 | 0.40 | 117 | 0.93 | 0.43 |
| 15 | 42.0 | 0.50 | 48.6 | 0.86 | 0.58 |
| 16 | 62.9 | 0.51 | 72.5 | 0.87 | 0.59 |

TABLE 10-continued

| Subject | SEP (mg/dL) | Correlation coefficient r | SDP (mg/dL) | SEP/SDP | Figure of merit |
|---|---|---|---|---|---|
| 17 | 76.5 | 0.62 | 96.2 | 0.80 | 0.78 |
| 18 | 46.1 | 0.45 | 50.9 | 0.91 | 0.50 |
| 19 | 47.0 | 0.52 | 53.6 | 0.88 | 0.59 |
| 20 | 45.7 | 0.45 | 50.3 | 0.91 | 0.49 |

The value of "r" can be included in the determination of the success rate by calculating the figure of merit, wherein the figure of merit is equal to r/(SEP/SDP). A successful prediction was arbitrarily fixed at a figure of merit cut-off value of 0.70. This figure of merit cut-off value is equivalent to the limit when (SEP/SDP) equals 0.90 and r equals 0.63. The underlined figure of merit values represent a more rigorous prediction of blood glucose level in the twenty diabetic subjects studied. Nine of twenty subjects showed successful prediction of blood glucose levels when this more rigorous figure of merit cut-off value was used. Thus, the sequential method, wherein a single optical head and the temperature programs described in this example were used, led to successful predictions of blood glucose levels.

Example 6

The device described in FIG. 3 was used in this example. The programmed temperature changes and the optical measurements were carried out at each of the two areas on the surface of the forearm as illustrated in FIG. 1. The body interface module 14 was placed on a table (not shown). The subject sat in front of the body interface module and the arm of the subject was placed on a cradle (not shown) that had been placed on the table. The two heads of the optical device were retracted by the subject's other hand. The two heads of optical device were then allowed to contact the skin and the data were collected from the time the heads contacted the skin. Data were collected at the two areas simultaneously; each area was subjected to a separate temperature program. Data from the two areas were used to derive a calibration relationship. The temperature program at the first area (the area closest to the elbow) was started at 30° C. and held at that temperature for 30 seconds; the temperature was then lowered to 22° C. at a rate of 2.67° C. per minute. The temperature program at the second area (the area farthest from the elbow) was started at 30° C. and held at that temperature for 30 seconds; the temperature was then raised to 38° C. at a rate of 2.67° C. per minute. Data (reflectance at four wavelengths and four distances) were collected for 210 seconds. The natural logarithm of each reflectance value at the two areas was determined. The values of Ln $R(\lambda_i, r_j, t)$ were fitted to the capillary blood glucose level values, as determined by a finger stick procedure, to generate a calibration relationship for each subject. The values used for the line fitting were measured at 30 seconds and 210 seconds after the two optical heads contacted the two areas of the skin. A four term linear model was calculated for each subject. A summary of the data is shown in Table 11. Nineteen of the twenty subjects tested in this example were different from the twenty subjects whose data are shown in Table 10. Subject No. 40 in Table 11 is the same as Subject No. 1 in Table 10. In Table 11, the standard error of prediction, which is the root means square calculated prediction error using leave-one-out cross validation method, is "SEP". The leave-one-out cross validation method is described in Wu et al., "Noninvasive Determination of Hemoglobin and Hematocrit Using a Temperature-Controlled Localized Reflectance Tissue Photometer", Analytical Biochemistry, 2000;287:284–293, incorporated herein by reference. The cross validation prediction correlation coefficient is "r", and the standard deviation of the 20 invasively-determined glucose values over the two days is "SDP". As defined in Example 5, the figure of merit is equal to r/(SEP/SDP).

TABLE 11

| Subject | SEP (mg/dL) | Correlation coefficient r | SDP (mg/dL) | SEP/SDP | Figure of merit |
|---|---|---|---|---|---|
| 21 | 54.4 | 0.60 | 67.9 | 0.80 | 0.75 |
| 22 | 76.50 | 0.55 | 92.1 | 0.83 | 0.67 |
| 23 | 60.4 | 0.66 | 80.6 | 0.75 | 0.89 |
| 24 | 52.0 | 0.75 | 78.3 | 0.66 | 1.13 |
| 25 | 21.6 | 0.72 | 31.8 | 0.68 | 1.06 |
| 26 | 76.50 | 0.76 | 118.7 | 0.64 | 1.17 |
| 27 | 59.1 | 0.58 | 72.1 | 0.82 | 0.71 |
| 28 | 36.6 | 0.65 | 47.3 | 0.77 | 0.84 |
| 29 | 60.1 | 0.66 | 78.9 | 0.76 | 0.86 |
| 30 | 70.3 | 0.68 | 96.4 | 0.73 | 0.93 |
| 31 | 64.8 | 0.53 | 75.3 | 0.86 | 0.61 |
| 32 | 40.3 | 0.55 | 47.8 | 0.84 | 0.65 |
| 33 | 43.3 | 0.38 | 46.4 | 0.93 | 0.41 |
| 34 | 26.7 | 0.80 | 44.5 | 0.60 | 1.33 |
| 35 | 29.9 | 0.58 | 35.9 | 0.83 | 0.70 |
| 36 | 21.9 | 0.47 | 24.2 | 0.91 | 0.52 |
| 37 | 42.3 | 0.69 | 57.9 | 0.73 | 0.94 |
| 38 | 62.0 | 0.63 | 78.6 | 0.79 | 0.80 |
| 39 | 52.4 | 0.72 | 76.4 | 0.69 | 1.06 |
| 40 | 56.7 | 0.48 | 61.7 | 0.92 | 0.52 |

It is possible to use the same criteria as for the determination of the success rate in the non-invasive measurement as was used in Example 5. The use of a (SEP/SDP) ratio of 0.9 yielded seventeen successful predictions of blood glucose levels out of twenty subjects. The successful predictions are designated by underlining. The use of the more rigorous figure of merit cut-off value, i.e., the figure of merit cut-off value being 0.7, achieved thirteen successful predictions of blood glucose levels out of twenty subjects.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for the determination of a disease state in a human subject, said method comprising the steps of:
   (a) measuring at least one optical property at a first area on a body part of said human subject to obtain a first set of data, said first area being subjected to a first temperature program;
   (b) measuring at least one optical property at a second area on said body part to obtain a second set of data, said second area being subjected to a second temperature program, said second temperature program being different from the first temperature program, said second area of said body part being morphologically similar to, adjacent to, but not substantially overlapping with said first area of said body part;
   (c) inserting said first set of data and said second set of data into a mathematical relationship to calculate a mathematical output; and
   (d) using said mathematical output with a decision rule to determine said disease state of said human subject, wherein said disease state is selected from the group consisting of diabetic state, dermal disease state, neoplasmic disease state, and vascular disease state.

2. The method of claim 1, wherein said optical properties are measured with light having a wavelength ranging from about 400 nm to about 2000 nm.

3. The method of claim 1, wherein said optical properties are measured by a diffuse reflectance technique.

4. The method of claim 1, wherein measuring steps (a) and (b) are performed simultaneously.

5. The method of claim 1, wherein measuring steps (a) and (b) are performed sequentially.

6. The method of claim 1, wherein said temperature programs employ temperatures ranging from about 10° C. to about 45° C.

7. The method of claim 1, wherein said mathematical relationship of step (c) is derived by a method comprising the steps of:
  (a) providing a population comprising a sufficient number of human subjects to establish a category selector, said population comprising a first sub-population comprising a sufficient number of human subjects in said disease state and a second sub-population comprising a sufficient number of human subjects not in said disease state;
  (b) for each of said number of human subjects in said population:
    (1) measuring at least one optical property at a first area on a part of an arm of each of said human subjects to obtain a first set of data, said first area being subjected to a first temperature program;
    (2) measuring at least one optical property at a second area on said part of said arm of each of said human subjects to obtain a second set of data, said second area on said part of said arm of each of said human subjects being subjected to a second temperature program, said second temperature program being different from the first temperature program, said second area of said part of said arm of each of said human subjects being morphologically similar to, adjacent to, but not substantially overlapping with said first area of said part of said arm of each of said human subjects; and
  (c) establishing a mathematical relationship between (i) said optical properties of said first set of data and said second set of data and
    (ii) said disease state.

* * * * *